United States Patent
Hirshowitz et al.

(10) Patent No.: US 10,589,091 B2
(45) Date of Patent: Mar. 17, 2020

(54) STATIC ELECTRICITY GENERATOR AND METHODS THEREOF

(71) Applicants: ELIACHAR TECHNOLOGIES DEVELOPMENT LTD, Haifa (IL); Bernard Hirshowitz, Haifa (IL)

(72) Inventors: Bernard Hirshowitz, Haifa (IL); Nir Lilach, Kfar Yehoshua (IL); Eliahu Eliachar, Haifa (IL)

(73) Assignee: ELIACHAR TECHNOLOGIES DEVELOPMENT LTD, Haifa (IL)

( * ) Notice: Subject to any disclaimer, the term of this patent is extended or adjusted under 35 U.S.C. 154(b) by 720 days.

(21) Appl. No.: 15/128,976

(22) PCT Filed: Mar. 25, 2015

(86) PCT No.: PCT/IL2015/050310
§ 371 (c)(1),
(2) Date: Sep. 25, 2016

(87) PCT Pub. No.: WO2015/145436
PCT Pub. Date: Oct. 1, 2015

(65) Prior Publication Data
US 2018/0193636 A1 Jul. 12, 2018

Related U.S. Application Data

(60) Provisional application No. 61/969,841, filed on Mar. 25, 2014.

(51) Int. Cl.
*A61N 1/00* (2006.01)
*A61N 1/10* (2006.01)
*H02N 1/04* (2006.01)

(52) U.S. Cl.
CPC ............... *A61N 1/10* (2013.01); *H02N 1/04* (2013.01)

(58) Field of Classification Search
CPC .................................. A61N 1/10; H02N 1/04
See application file for complete search history.

(56) References Cited

U.S. PATENT DOCUMENTS 2,644,903 A 7/1953 Lehrer

FOREIGN PATENT DOCUMENTS

| EP | 0975911 A1 | 2/2000 |
| EP | 1177812 A1 | 2/2002 |
| RU | 24273371 C1 | 1/2013 |
| WO | 2015/145436 A1 | 10/2015 |

OTHER PUBLICATIONS

International Search Report of PCT/IL2015/050310, dated Jul. 22, 2015.

(Continued)

*Primary Examiner* — Mallika D Fairchild

(57) ABSTRACT

The present invention provides a portable handheld static-electricity generator and a method thereof for alleviating pain in at least one portion of patient's body, comprising: a movable brush, a polymer assembly comprising a rubbing-surface portion upon which the brush rubs and an automatically-operated mechanical unit. The polymer assembly having affinity to a defined charge such that when the movable brush rubs the rubbing-surface of the polymer assembly for a predefined time a static electricity is generated.

20 Claims, 10 Drawing Sheets

(56) References Cited

OTHER PUBLICATIONS

Written Opinion of the International Search Authority of PCT/IL2015/050310, dated Jul. 22, 2015.
International Preliminary Report on Patentability of PCT/IL2015/050310, dated Aug. 17, 2016.
Supplementary European Search Report of EP 15768231, dated Nov. 13, 2017.
Office action from corresponding Chinese application, 201580027285.0, dated Mar. 28, 2019.

STATIC ELECTRICITY GENERATOR AND METHODS THEREOF

CROSS REFERENCE TO RELATED APPLICATIONS

This application is a U.S. National Phase filing under 35 U.S.C. 371 of International (PCT) Patent Application No. PCT/IL2015/050310, filed 25 Mar. 2015, which claims priority from U.S. Provisional Patent Application No. 61/969,841, filed 25 Mar. 2014, both of which are incorporated by reference in their entirety.

FIELD OF THE INVENTION

The present invention generally pertains to a static electricity generator and to methods thereof. More specifically, the invention relates to a medical device useful for decreasing pain of a patient by means of a static electricity generator and to method of alleviating said pain.

BACKGROUND OF THE INVENTION

Myalgia (muscle pain) and joint paint are each a common symptom of many diseases and disorders. Many treatments were suggested art to alleviate the pain, including application of heat and electricity upon the sour organ, and using static electricity, see for example EP1177812. Various methods devices for discharging static electricity were suggested, see e.g., EP 0975911, yet none of them introduces a static electricity generator which is effectively alleviating pain.

SUMMARY OF THE INVENTION

It is an object of the present invention to disclose a portable handheld static-electricity generator for alleviating pain in at least one portion of patient's body. The aforesaid generator comprises: (a) an electret polymer assembly having a rubbing-surface; (b) a brush movable over said rubbing-surface, (c) an automatically-operated mechanical unit displacing said brush relative to said electret polymer assembly.

It is a core purpose of the present invention to disclose the generator comprising a brush lifting element carrying said brush. The brush lifting element has a first position and second position; in said first position, said brush is in mechanical contact with said electret polymer assembly; in said second position, there is no mechanical contact therebetween.

It is another object of the present invention to disclose the defined charged which is positive charge or negative charge.

It is a further object of the present invention to disclose the polymer assembly with affinity to negative charge; said brush is with affinity to positive charge.

It is a further object of the present invention to disclose the mechanical unit comprising a DC motor and gear-head thereof, provided in connection with a spur gear by means of a worm gear.

It is a further object of the present invention to disclose the brush assembly comprising a brushing material and a brush body; said brushing material which is affixed to said brush body.

It is a further object of the present invention to disclose the brush which is at least reversibly affixed on said spur gear.

It is a further object of the present invention to disclose the polymer sheet assembly comprising said rubbing-surface portion as an upper portion upon which the static electricity which is generated and a lowest surface portion attached to said patient's body, through which the charge is discharged.

It is a further object of the present invention to disclose the polymer sheet assembly adjacent to said brush member such that by operating said motor, said spur gear activates said brush which is continuously rubbing said rubbing-surface portion of said polymer sheet assembly for a predefined time, thereby generating static electricity upon said polymer sheet assembly by attaching said charged sheet assembly to said patient's body thereby, pain is alleviated.

It is a further object of the present invention to disclose the brush activated in a linear motion, semicircle motion, lead screw motion or turning motion.

It is a further object of the present invention to disclose the mechanical unit generating continuous or in pulse-wise manner a negative static electrical charge density ranging between about 0.1 and about 20 kilo Volts per square inch.

It is a further object of the present invention to disclose a polymer assembly composed of a material selected from the group consisting of silicone rubber, silicon, Teflon, PVC, polyethylene, rubber, Butyl rubber, Hypalon rubber, Santoprene rubber, Epichlorohydrin rubber, Latex rubber, PET, Polyimide, Polystyrene, Cellulose nitrate and any combination thereof.

It is a further object of the present invention to disclose the brush is composed of a material selected from the group consisting of Polyurethane foam, hair, nylon, Nylatron, glass, paper cotton and any combination thereof.

It is a further object of the present invention to disclose predefined time period (t) ranging from one or more ranges selected from a group consisting of 1 to 45-120 seconds; 1 to 12-44 seconds. 0.5 to 1-11 seconds, 1-3 to 6-12 seconds, 4-6 to 8-12 seconds and any combination thereof.

It is a further object of the present invention to disclose a method of generating an electro-static field, wherein comprising steps of: (a) providing a portable handheld static-electricity generator comprising a movable brush, a polymer sheet assembly comprising a rubbing-surface; and an automatically-operated mechanical unit displacing said brush relative to said electret polymer assembly; said generator comprises a brush lifting element carrying said brush; said brush lifting element has a first position and second position; in said first position, said brush is in mechanical contact with said electret polymer assembly; in said second position, there is no mechanical contact therebetween; (b) (b) displacing said brush in respect to said polymer sheet thereby, rubbing said polymer assembly by means of said brush; (c) alternately positioning said brush in said first and second position such that an electric charge is generated and said electric charge leaks to a patient's body, respectively; (d) generating a pulse electro-static field; and (e) attaching said polymer sheet to said portion of patient's body.

It is a further object of the present invention to disclose the step of providing said polymer sheet assembly having affinity to negative charge or positive charge.

It is a further object of the present invention to disclose the step of attaching comprising step of discharging said electro-static upon said portion of patient's body.

It is a further object of the present invention to disclose the step of generating said static electricity is activated along a predefined period t.

It is a further object of the present invention to disclose the step of actuating said brush in a linear motion, semicircle motion, lead screw motion or turning motion.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF THE INVENTION

A portable handheld static-electricity generator for alleviating pain in patient's portion of body is hereby presented in a non-limiting manner. This electro-static field generating medical device is characterized by a movable brush and rubbing-surface upon which said brushed rubs such that static electricity is generated.

The term "silicone" broadly refers hereinafter, in a non-limiting manner, a sheeting, beads or pieces of rubber, plastic, glass, pith, and polymer in any form which is made from inert, non-reactive silicone, for example polydimethylsiloxane or related polysiloxane materials (represented generally by the structure $R_2SiO$, where R is a monovalent organic radical, including for example a methyl, ethyl, propyl or phenol group, among others and which may be several thousands of S—O units or more in length and that can build up static electricity on it.

According to one embodiment of the invention, this medical device is characterized by an automatically-operated mechanical unit and a silicone sheet assembly. The mechanical unit comprising a DC motor and gear-head thereof, provided in connection with a spur gear by means of a worm gear. A brush assembly, comprises a brushing member made of Kevlar, rubber, fabric, leather or any other suitable material and a brush body, is reversibly or irreversibly attached on the spur gear. The silicone sheet assembly comprises a silicone sheet and base thereof. This sheet is shape in a suitable manner: a planer sheet or 3D designed one (e.g., with a concaved or polygonal structure etc.), smooth or with textured surface etc. This silicone sheet is positioned adjacent to the brushing member, pressed against the silicone sheet inner surface by a spring such that by operating the motor, the spur gear circulates the brush, which is continuously rubbing the silicone sheet for a predefined time t, thereby generating static electricity upon the sheet, by attaching the electrically-loaded silicone sheet to a patient's portion of body, pain is alleviated. The attachment force of the brush to the silicone sheet, which determine the friction and the resultant electrostatic field, can be adjusted by selecting the preferred spring.

The mechanical device, together with the battery pack is placed within a specialized fabric structure, which attaches the mechanical unit and the battery pack to the patient's body.

Figure 1A:
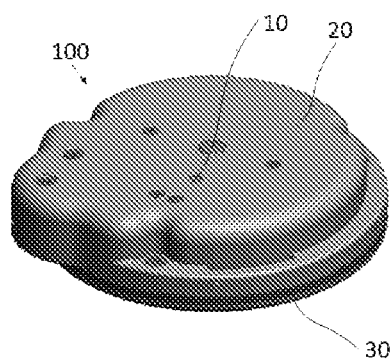
FIGS. 1a to 1c are prospective general, top and bottom views of a portable handheld static-electricity generator, respectively.
Figure 1B:
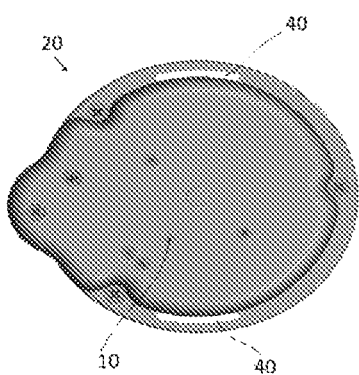
Figure 1C:
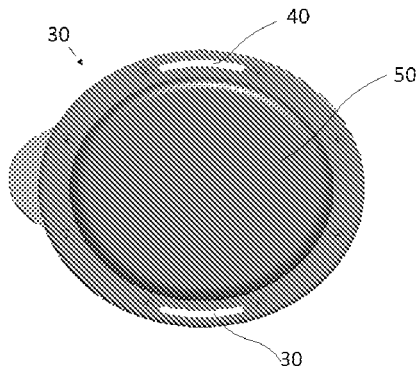

An embodiment of the invention is hereby schematically illustrated in a non-limiting manner:

Reference is now made to FIGS. 1a to 1c, showing general, top and bottom views of a portable handheld static-electricity generator 100, respectively. Upper cover 10 encloses an electric drive moving a brush over silicon sheet an internal side of silicone sheet 50. In FIG. 1c, an external side of silicone sheet 50 is visually available. Numeral 40 refers to slots for straps securing generator 100 to the patient's body (not shown). LED is designed for indicating an operating mode of generator 100.

Figure 2:
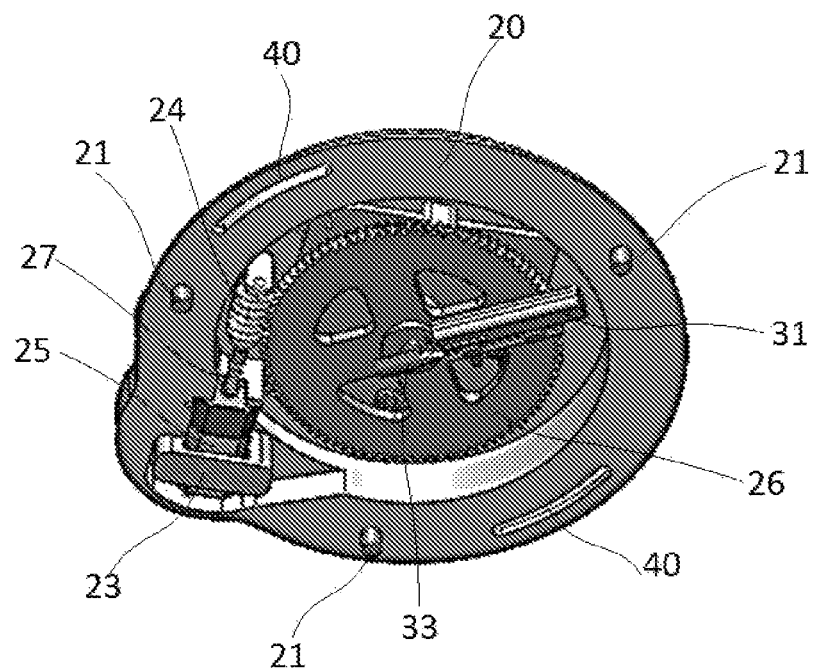
FIG. 2 is an internal prospective view of an upper cover of a portable handheld static-electricity generator.

Reference is now made FIG. 2, presenting an internal prospective view of an upper cover of portable handheld static-electricity generator 100. Electric motor 25 secured by a clamp 23 energized by an electric battery (not shown). Rotation from electric motor 25 is transferred to screw 24 via shaft 27. Screw 24 is coupled with cogwheel 26.

Figure 3:
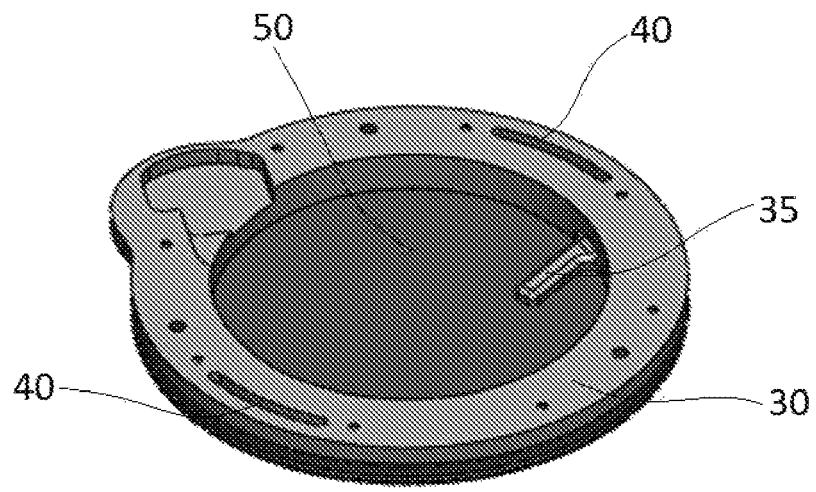
FIG. 3 is an internal prospective view of a lower cover of a portable handheld static-electricity generator.

Reference is now made to FIG. 3 presenting an internal prospective view of lower cover 30 of portable handheld static-electricity generator 100. Numeral 35 refers to a brush lifter. Operation principle will be explained below.

Figure 4:
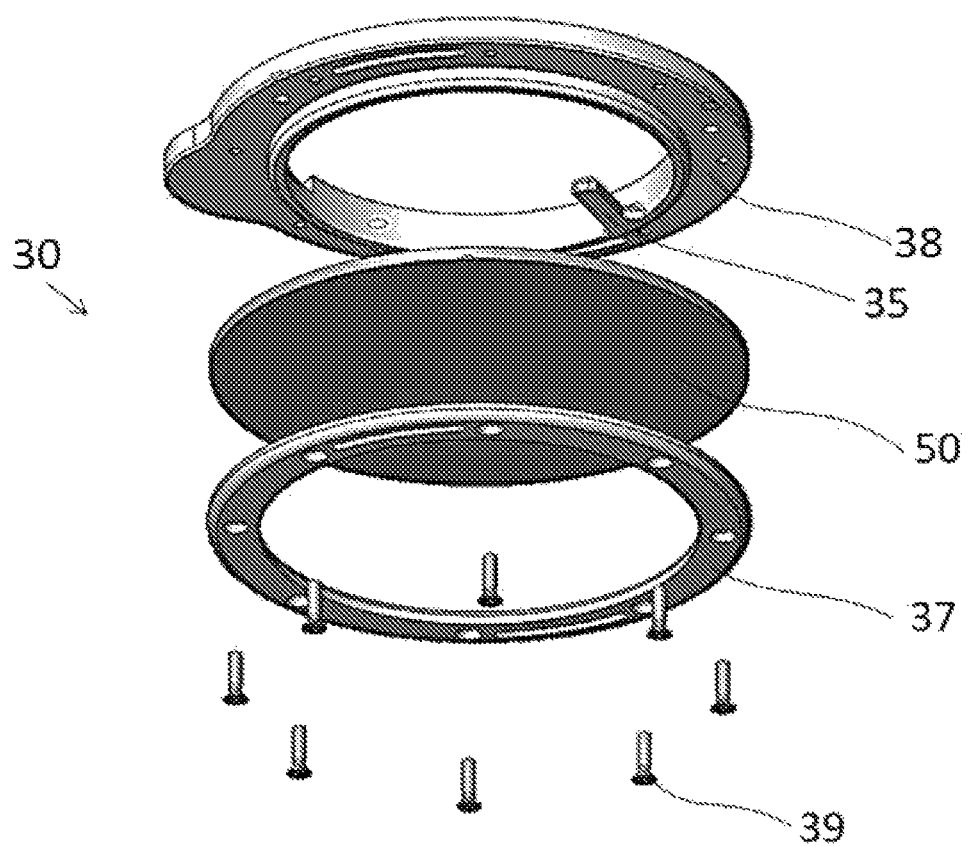
FIG. 4 is an exploded view of a lower cover.

Reference is now made to FIG. 4 presenting lower cover 30 is formed by a two rings 37 and 38 between which silicone sheet 50 is secured. Screws 39 mechanically interconnect two rings 37 and 38.

Figure 5A:
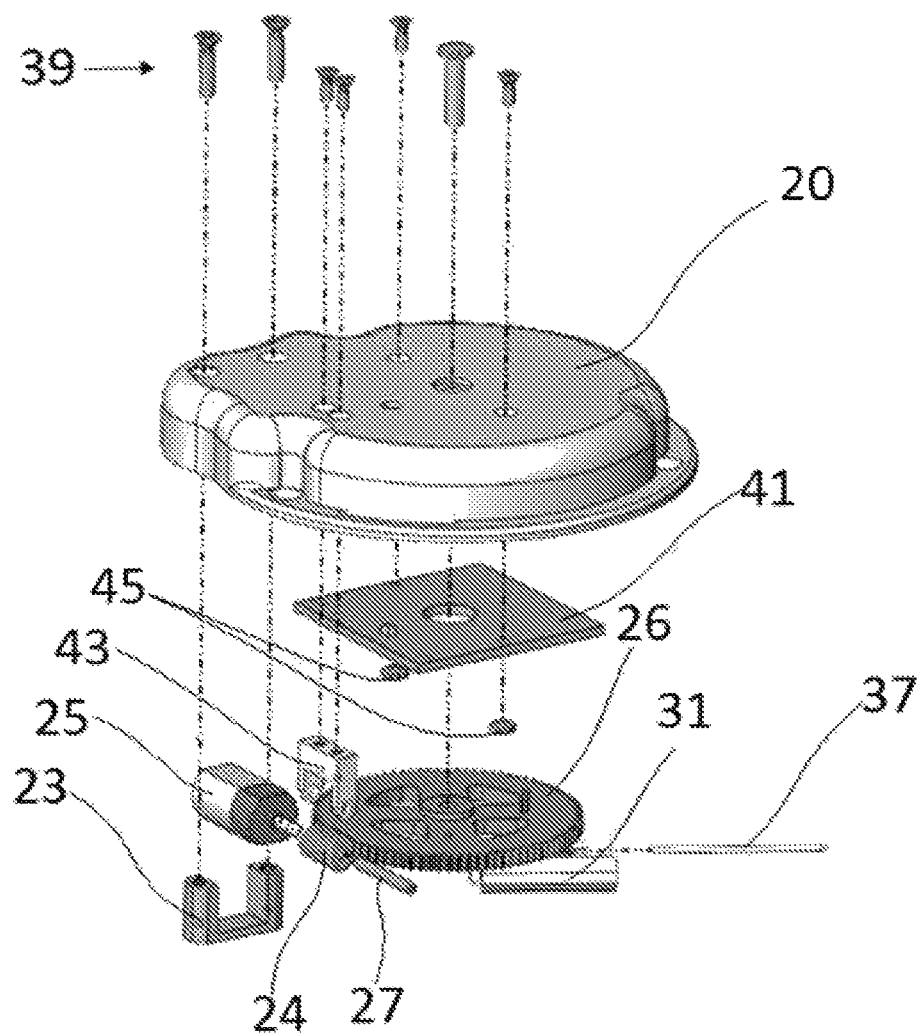
FIGS. 5a and 5b are exploded views of an electric drive at different aspects.
Figure 5B:
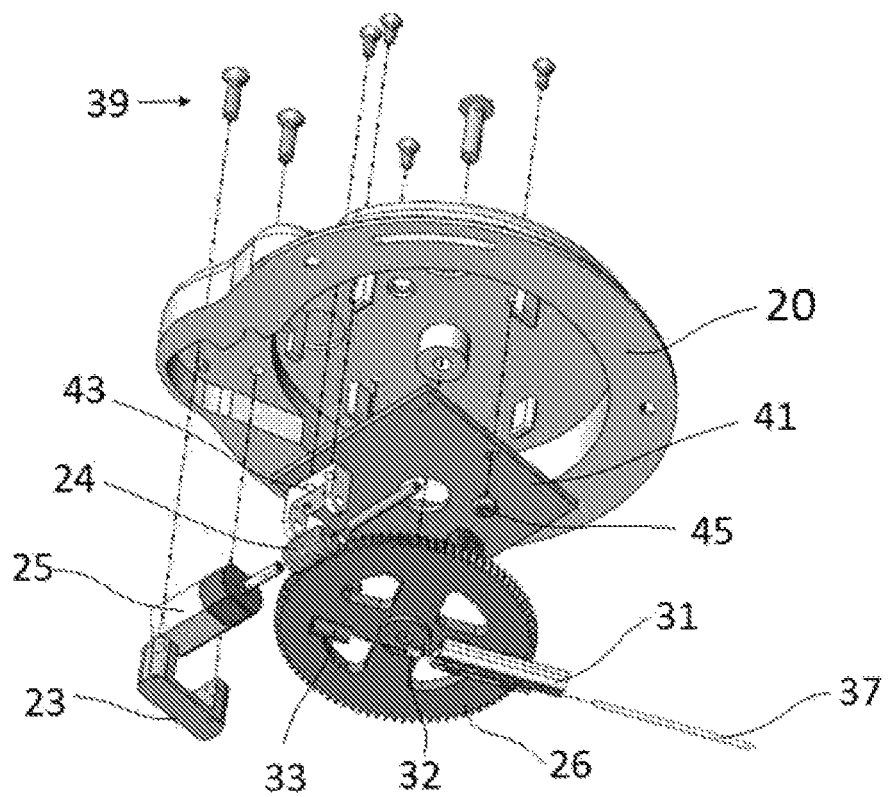

Reference is now made to FIGS. 5a and 5b presenting exploded views of an electric drive at different aspects. As described above, electric motor 25 rotates screw 24 coupled with cogwheel 26. The aforesaid cogwheel 26 carries brush 31 which moves together with cogwheel 26. Specifically, brush 31 is pivoted on axis 37. Numeral 41 refers to a printed circuit board (PCB) functioning as a control card. PCB 41 is secured to upper cover 20 by means of screws 39 and nuts 45. Brush 31 is forced to silicone sheet 50 by spring 32 secured by a stopper 33.

Figure 6A:
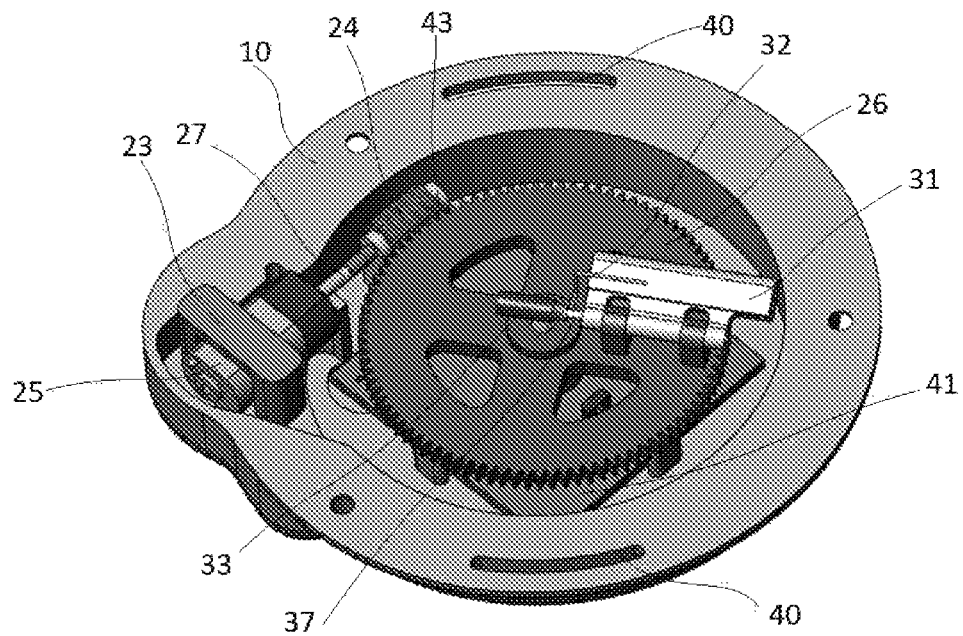
FIGS. 6a and 6b are assembled views of an electric drive at different aspects.
Figure 6B:
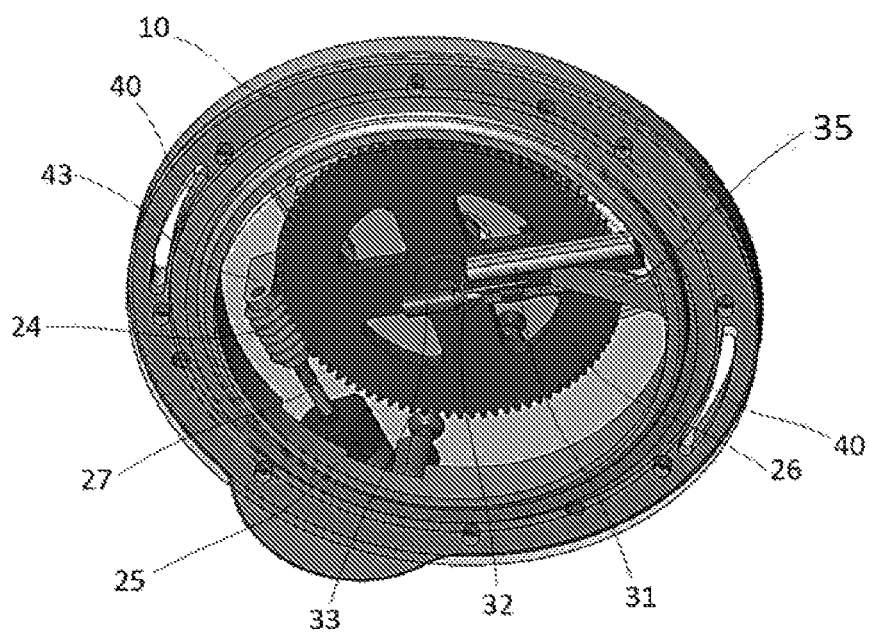

Reference is now made to FIGS. 6a and 6b. presenting the assembled views of an electric drive at different aspects. When brush 31 rotating together with cogwheel 26 encounters lifter 35 and angularly displaced relative to cogwheel 26 and detaches from silicone sheet 50.

Figure 7:
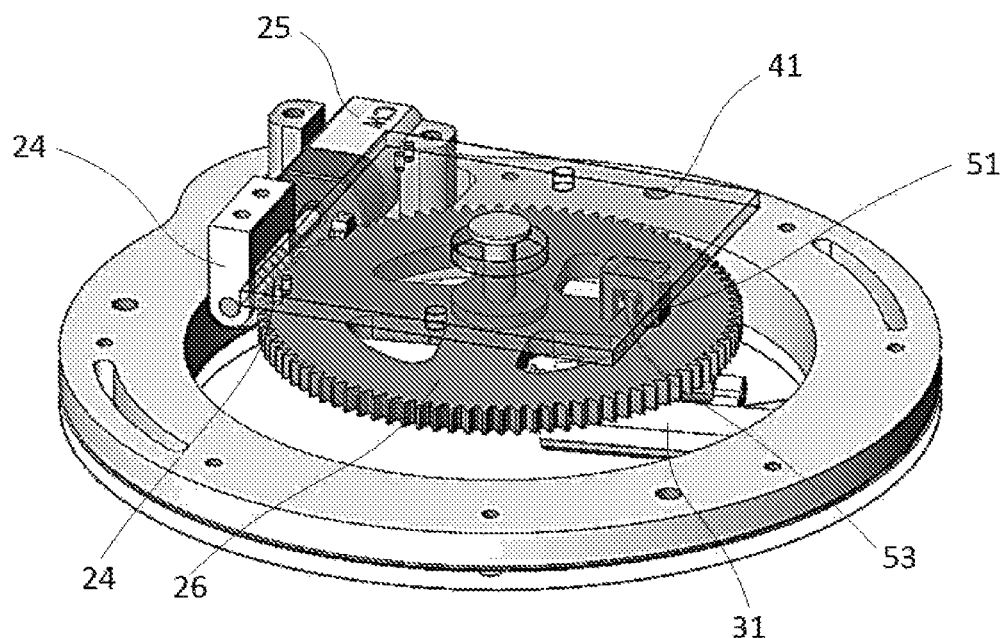
FIG. 7 illustrates operation of an optical microsensor.
Figure 8:
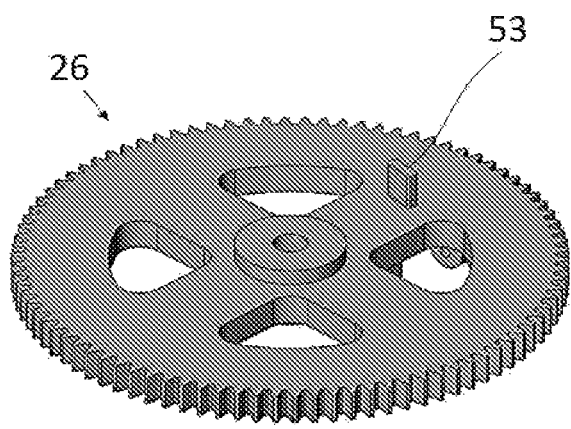
FIG. 8 is a prospective view of a cogwheel.

Reference is now to FIGS. 7 and 8 illustrating operation of photo-microsensor 51 constituting an optoelectronic pair of a light source and a light detector (not shown). A member 53 carried by cogwheel 26 blocks a light beam from the light source to the light detector and electric motor 25 is stopped. End of session: According to an embodiment of the invention, the session lasts about t seconds; t is ranging, for example, from 4 to 8 seconds; whereas t can be modified by the patient or by his/her physician. By the end of the session, the brush needs to be detached from the silicone sheet. This is achieved by the following: after predefined duration or otherwise by means of an online-feedback manner lasting t seconds, the brush meets a brush lifter, which detach it from the silicone sheet. At the same time, a 'fin' from the spur gear get into the photo-microsensor which notify the software that the brush has been detached and the motor is stopped.

Example 1

According to an embodiment of the invention, a method for alleviating pain in patient's body or a portion thereof is presented: The method comprises, inter alia, steps of (a) providing a portable handheld static-electricity generator as defined in any of the above, which comprises, inter alia, a movable brush and a rubbing-surface upon which the brushed rubs; (b) actuating the brush in respect to the sheet thereby rubbing the sheet by means of the brush; (c) generating a static electricity (electro-static field); and (d) attaching the sheet to patient's body so that pain is alleviated.

Figure 9:
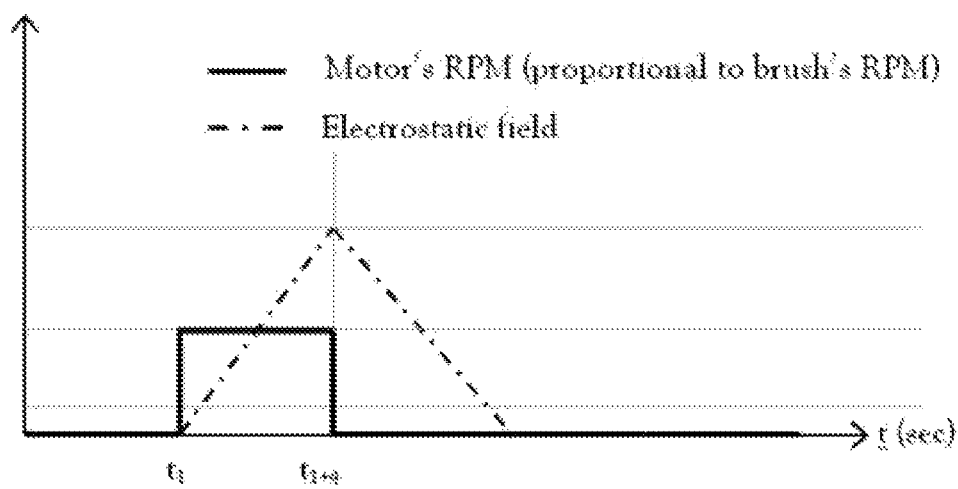
FIGS. 9 to 13 are graphs showing time dependences of motor rpm and electrostatic field intensity for different working modes of a portable handheld static-electricity generator.

Daily operation of the portable handheld static-electricity generator as defined in the aforesaid embodiment in 8 sessions per day, 4 seconds each, alleviates joint pain and improves Wong-Backer Face Scale in one unit after one week. Graphs of RPM and electric field in each session are shown in FIG. 9.

Example 2

Figure 10:
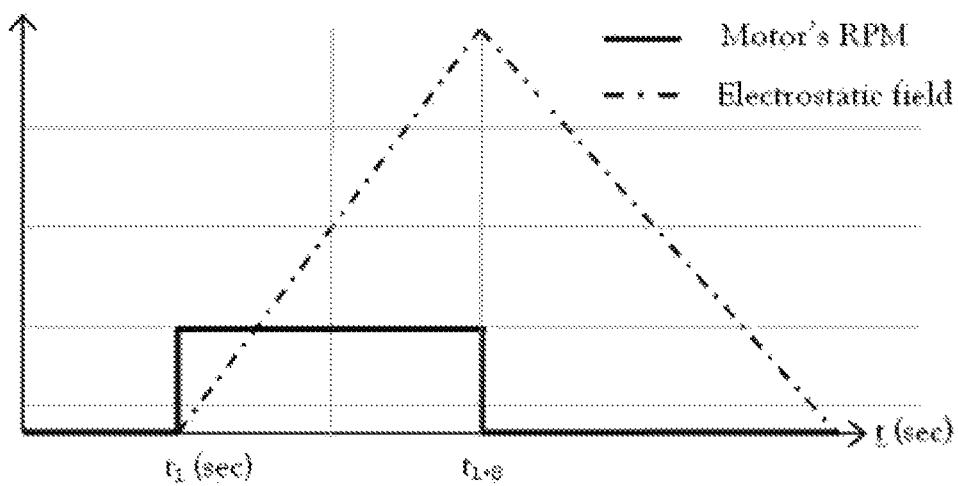

Daily operation of the portable handheld static-electricity generator as defined and described in the aforesaid embodiment in 6 sessions per day, 8 seconds each (a continuous electrostatic field), alleviates muscle pain and improves Wong-Backer Face Scale in one unit after one week of treatment. Graphs of RPM and electric field in each session are shown in FIG. 10.

Example 3

Figure 11:
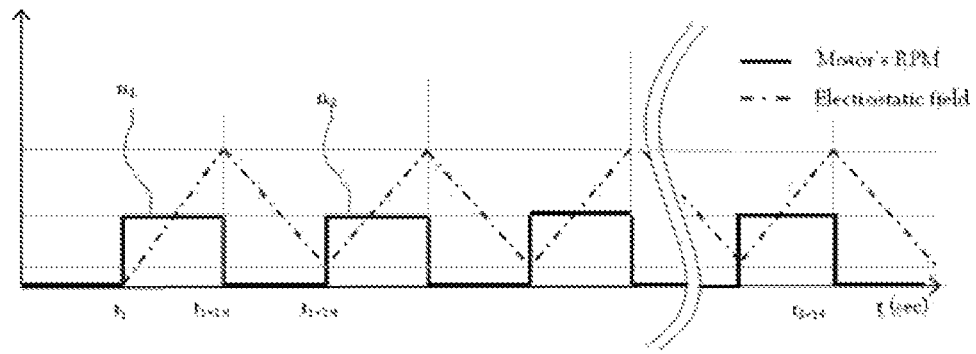

Daily operation of the portable handheld static-electricity generator as defined and described in aforesaid embodiment in 6 sessions per day, 14 seconds each (each session comprises introduction of a pulsed electrostatic field, n=10), alleviates muscle pain and improves Wong-Backer Face Scale in one unit after one week of treatment. Graphs of RPM and electric field in each session are shown in FIG. 11.

Example 4

Figure 12:
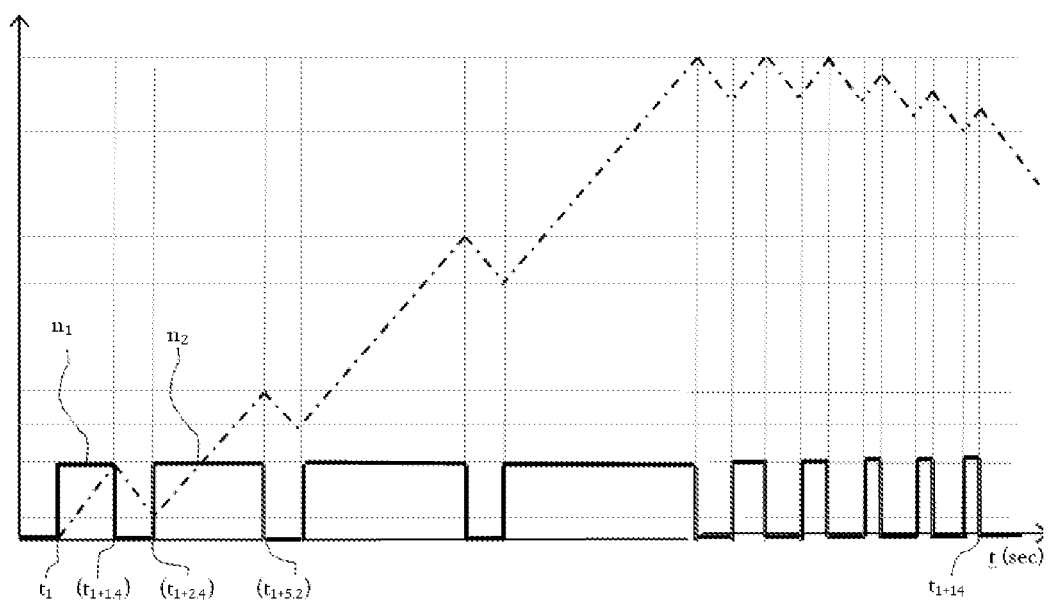
Figure 13:
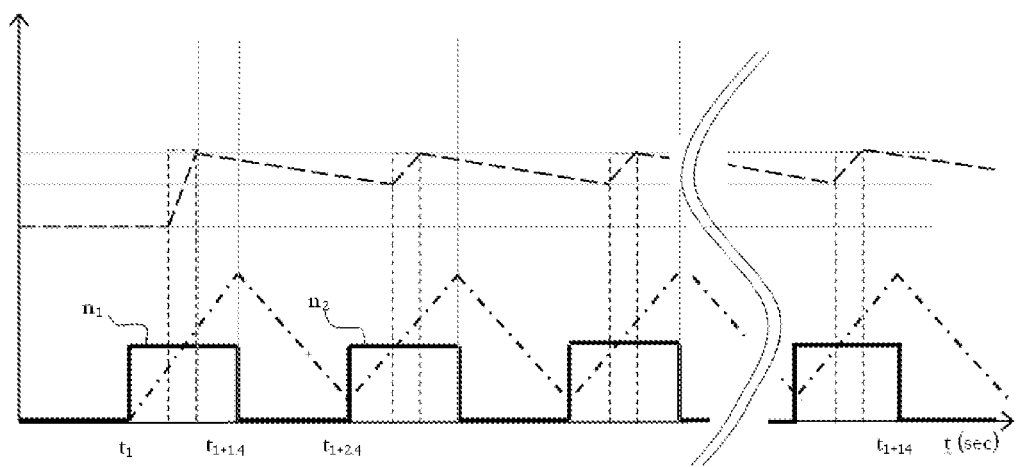

Daily operation of the portable handheld static-electricity generator as defined and described in aforesaid embodiment and further comprising electrical means for regulating electrostatic field (coil, capacitor etc) in 4 sessions per day, each treatment provides for 14 seconds (at least half of the sessions include introduction of a pulsed electrostatic field, n=9), alleviates joint pain and improves Wong-Backer Face Scale in one unit after one week of treatment. Graphs of RPM and electric field in each session are shown in FIG. 12.

Example 5

Daily operation of the portable handheld static-electricity generator as defined and described above, which further comprise an infrared light emitter, and further comprising electrical means for regulating electrostatic field (coil, capacitor etc) in 4 sessions per day, each treatment provides for 14 seconds (at least half of the sessions include introduction of a pulsed electrostatic field, n=9), alleviates joint pain and improves Wong-Backer Face Scale in one unit after one week of treatment. Graphs of RPM and electric field in each session are shown in FIG. 9.

Example 6

Another object of the present invention is to provide means and methods of a non-invasive treatment for chronic pain relief by utilizing a semi conductive diaphragm of occlusive silicone sheeting of a thickness between about 2 and 4 mm thickness.

Hence according to an embodiment of the invention, an attached mechanism generates in either a continuous or pulse-wise manner a negative static electrical charge of about 10 to about 20 kilowatts per square inch that is applied to the silicone, providing large amount of negative ions that are being used for treatment.

The continuous charge of ions avoids electrical charge decay due to environmental and patient conditions such as humidity, temperature and perspiration. The negative ions on the silicone repel circulating negatively charged components on the painful area of the body surface over which the device is applied and attract positively charged components, as a result of which a beneficial effect on pain will be accrued.

A pain scale measures a patient's pain intensity or other features. Pain scales are based on self-report, observational (behavioral), or physiological data. Self-report is considered primary and should be obtained if possible (since pain is a quale by definition, and therefore assessment based on any set scale of expected outcomes from similar cases can fail to provide useful clinical data). Wong-Baker FACES pain rating scale, for example, shows a series of faces ranging from a happy face at 0, "No hurt" to a crying face at 10 "Hurts worst".

A set of three different devices are useful for pain relief by reducing Wong-Baker FACES pain rating scale in at least one unit (n=23). In a first device, static electricity density of 15 KV per square inch is applied to a semi conductive material such as silicone sheeting as a barrier; in a second system, a static electricity density of 15 KV per square inch that is gradually released from a silicone sheeting to a Human's skin; and in a third system, a static electricity device that generates about 10 to about 20 KV per square inch according to a predefined protocol (see e.g., Example 5).

The invention claimed is:

1. A portable static-electricity generator for alleviating pain in at least one portion of patient's body, comprising
   a. an electret polymer assembly having a rubbing-surface;
   b. a brush movable over said rubbing-surface,
   c. an automatically-operated brush lifter displacing said brush relative to said electret polymer assembly;
      wherein said generator comprises a brush lifting element carrying said brush; said brush lifting element has a first position and second position; in said first position, said brush is in mechanical contact with said electret polymer assembly; in said second position, there is no mechanical contact therebetween.

2. The static-electricity generator of claim 1, wherein a charge generated by said static-electricity generator is positive charge or negative.

3. The static-electricity generator of claim 1, wherein when said polymer assembly has an affinity to negative charge; said brush is has an affinity to positive charge.

4. The static-electricity generator of claim 1, wherein said brush lifter comprising a DC motor and gear-head thereof, said gear-head comprises a spur gear a worm gear.

5. The static-electricity generator of claim 4, wherein said brush is at least reversibly affixed on said spur gear.

6. The static-electricity generator of claim 4, wherein said electret polymer assembly is adjacent to said brush member such that by operating said motor, said spur gear activates said brush which is continuously rubbing said rubbing-surface portion of said electret polymer assembly for a predefined time, thereby generating static electricity upon said electret polymer assembly; said electret polymer assembly in a charged condition is attachable to said patient's body for a predetermined time period t for pain alleviation.

7. The static-electricity generator of claim 6, said predefined time period t ranges from one or more ranges selected from a group consisting of 1 to 45-120 seconds, 1 to 12-44 seconds, 0.5 to 1-11 seconds, 1-3 to 6-12 seconds, 4-6 to 8-12 seconds and any combination thereof.

8. The static-electricity generator of claim 1, wherein said brush assembly comprises a brushing material and a brush body; said brushing material is affixed to said brush body.

9. The static-electricity generator of claim 1, wherein said electret polymer assembly comprises said rubbing-surface portion as an upper portion upon which the static electricity is generated and a lower surface portion attachable to said patient's body, through which the charge is discharged.

10. The static-electricity generator of claim 1, wherein said brush is activated in a linear motion, semicircle motion, lead screw motion or turning motion.

11. The static-electricity generator of claim 1, wherein said brush lifter generates in a continuous or a in pulse-wise manner a negative static electrical charge density ranging between 0.1 and 20 kilo Volts per square inch.

12. The static-electricity generator of claim 1, wherein said a polymer assembly is composed of a material selected from the group consisting of silicone rubber, silicon, Teflon, PVC, polyethylene, rubber, Butyl rubber, Hypalon rubber, Santoprene rubber, Epichlorohydrin rubber, Latex rubber, PET, Polyimide, Polystyrene, Cellulose nitrate and any combination thereof.

13. The static-electricity generator of claim 1, wherein said brush is composed of a material selected from the group consisting of Polyurethane foam, hair, nylon, Nylatron, glass, paper cotton and any combination thereof.

14. A method of generating an electro-static field, wherein comprising steps of:
  a. providing a portable static-electricity generator comprising a movable brush, a polymer sheet assembly comprising a rubbing-surface; and an automatically-operated brush lifter displacing said brush relative to said electret polymer assembly; said generator comprises a brush lifting element carrying said brush; said brush lifting element has a first position and second position; in said first position, said brush is in mechanical contact with said electret polymer assembly; in said second position, there is no mechanical contact therebetween;
  b. displacing said brush in respect to said polymer sheet thereby, rubbing said polymer assembly by means of said brush;
  c. alternately positioning said brush in said first and second position such that an electric charge is generated and said electric charge leaks to a patient's body, respectively;
  d. generating a pulse electro-static field; and
  e. attaching said polymer sheet to said portion of patient's body for a predetermined time period t.

15. The method according to claim 14, wherein at least one of the following is true:
  a. said step of providing said polymer sheet assembly having affinity to negative charge or positive charge;
  b. said step of attaching said polymer sheet comprises step of discharging said electro-static field upon said portion of patient's body;
  c. said step of generating said static electricity is activated along a predefined period t.

16. The method according to claim 14, wherein said step of actuating said brush comprises moving the brush in a linear motion, semicircle motion, lead screw motion or turning motion.

17. The method according to claim 14, wherein said predetermined time period t ranges from one or more ranges selected from a group consisting of 1 to 45-120 seconds; 1 to 12-44 seconds, 0.5 to 1-11 seconds, 1-3 to 6-12 seconds, 4-6 to 8-12 seconds and any combination thereof.

18. The method according to claim 17, wherein said portable static-electricity generator provides a train of n pulses of static-electricity, n is integer equal or greater 2.

19. The method according to claim 18, wherein at least two pulses from said n pulses of static-electricity are of equal duration or electrostatic field.

20. The method according to claim 17, wherein at least two pulses from said n pulses of static-electricity are of different duration or electrostatic field.

\* \* \* \* \*